(12) United States Patent
He et al.

(10) Patent No.: US 6,432,683 B1
(45) Date of Patent: Aug. 13, 2002

(54) PREPARATION OF 2-AMINOMUCONATE FROM 2-AMINOPHENOL BY COUPLED ENZYMATIC DIOXYGENATION AND DEHYDROGENATION REACTIONS

(75) Inventors: Zhongqi He, Bangor, ME (US); Jim C. Spain, Panama City, FL (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/664,974

(22) Filed: Sep. 18, 2000

Related U.S. Application Data

(60) Provisional application No. 60/205,916, filed on May 22, 2000.

(51) Int. Cl.$^7$ ................................................ C12P 13/04
(52) U.S. Cl. ..................................................... 435/106
(58) Field of Search ......................................... 435/106

(56) References Cited

PUBLICATIONS

S.F. Nishino, J.C. Spain, Degradation of Nitrobenzene by a *Pseudomonas pseudoalcaligenes*, Applied and Environmental Microbiology, Aug. 1993, p. 2520–2525. Published: Aug. 1993.

U. Lendenmann, J.C. Spain, 2–Aminophenol 1,6–Dioxygenase: a Novel aromatic Ring Cleavage Enzyme Purified from *Pseudomonas pseudoalcaligenes* JS45, Journal of Bacteriology, Nov. 1996, p. 6227–6232. Published: Nov. 1996.

Z. He, J.C. Spain, A Novel 2–Aminomuconate Deaminase in the Nitrobenzene Degradation Pathway of *Pseudomonas pseudoalcaligenes* JS45, Journal of Bacteriology, May 1998, p. 2502–2506. Published: May 1998.

Z. He, J.K. Davis, J.C. Spain, Purification, Characterization and Sequence Analysis of 2–Aminomuconic 6–Semialdehyde Dehydrogenase from *Pseudomonas pseudoalcaligenes* JS45, Journal of Bacteriology, Sep. 1998, p. 4591–4595. Published: Sep. 1998.

J.K. Davis, Z. He, C.C. Somerville, J.C. Spain, Genetic and biochemical comparison of 2–aminophenol 1,6–dioxygenase of *Pseudomonas pseudoalcaligenes* JS45 to meta–cleavage dioxygenases: divergent evolution of 2–aminophenol meta–cleavage pathway, Arch Microbiol (1999) 172:330–339. No publication date shown.

Z. He, J.C. Spain, Preparation of 2–aminomuconate from 2–aminophenol by coupled enzymatic dioxygenation and dehydrogenation reactions, Journal of Industrial Microbiology & Biotechnology (1999) 23, 138–142. Published after Jun. 9, 1999. (date of acceptance).

*Primary Examiner*—Sandra E. Saucier
(74) *Attorney, Agent, or Firm*—Charles E. Bricker; Thomas L. Kundert

(57) ABSTRACT

A method for the preparation of 2-aminomuconate which comprises adding 2-aminophenol to a mixture of 2-aminophenol 1,6-dioxygenase, 2-aminomuconic semialdehyde dehydrogenase and NAD$^+$ (nicotinamide adenine dinucleotide, oxidized form) in a buffer, and recovering a fraction containing 2-aminomuconate from the mixture.

3 Claims, No Drawings

PREPARATION OF 2-AMINOMUCONATE FROM 2-AMINOPHENOL BY COUPLED ENZYMATIC DIOXYGENATION AND DEHYDROGENATION REACTIONS

This application claims priority from Provisional application Ser. No. 60/205,916, filed May 22, 2000.

RIGHTS OF THE GOVERNMENT

The invention described herein may be manufactured and used by or for the Government of the United States for all governmental purposes without the payment of any royalty.

BACKGROUND OF THE INVENTION

The present invention relates to the preparation of 2-aminomuconate from 2-aminophenol.

2-Aminomuconate is an intermediate in the oxidative metabolism of tryptophan in mammals. The compound is not commercially available, and studies of its metabolism have been prevented by the lack of a chemical synthesis and the instability of the molecule.

Interest in the catabolic pathway of degradation of L-tryptophan has grown steadily over the last decade due to the role of quinolinate and other metabolites in several neuropathological conditions. The neurotoxin, quinolinate, is formed nonenzymatically from 2-amino-3-carboxymuconic semialdehyde in mammalian tissues. 2-Amino-3-carboxymuconic semialdehyde is enzymatically converted to 2-aminomuconate (2-aminohexa-2,4-diene-1, 6-dioate), via 2-aminomuconic semialdehyde. The effect of the enzymatic pathway on non-enzymatic accumulation of quinolinate in the central nervous system has not been investigated. Furthermore, 2-aminomuconate itself may also have a significant neurophysiological function in the central nervous system by virtue of the fact it is a dicarboxylic α-amino acid, and is similar to other neural excitatory amino acid agonists or antagonists. Another concern is the neurotoxicity of ammonia, released from 2-aminomuconate during the metabolism of tryptophan in the central nervous system. The lack of the availability of 2-aminomuconate has severely limited experimental approaches to investigation of these aspects of mammalian neurophysiology.

Recently, we found that 2-aminomuconate is one of the intermediates in the pathway for the biodegradation of nitrobenzene by the bacterium *Pseudomonas pseudoalcaligenes* JS45. 2-Aminomuconate is produced from 2-aminophenol by the action of 2-aminophenol 1,6-dioxygenase and 2-aminomuconic semialdehyde dehydrogenase. We have prepared 2-aminomuconate with these two enzymes either in crude extracts or in the fractions from a DEAE-Sepharose column, and separated it by anion exchange chromatography for use in investigating the properties of 2-aminomuconate deaminase from *P. pseudoalcaligenes* JS45. However, attempts to prepare the material in large quantities for general use failed because the partially purified dioxygenase was unstable even during storage at −70° C. In crude extracts the dioxygenase was relatively stable, but the presence of 2-aminomuconate deaminase precluded accumulation of 2-aminomuconate.

Accordingly, it is an object of the present invention to provide an improved method for the preparation of 2-aminomuconate.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there is provided an improved method for the preparation of 2-aminomuconate. The method of this invention comprises adding 2-aminophenol to a mixture of 2-aminophenol 1,6-dioxygenase, 2-aminomuconic semialdehyde dehydrogenase and AND+ (nicotinamide adenine dinucleotide, oxidized form) in a buffer, and recovering a fraction containing 2-aminomuconate from the mixture.

DETAILED DESCRIPTION OF THE INVENTION

2-Aminomuconic semialdehyde dehydrogenase was obtained from *Pseudomonas pseudoalcaligenes* JS45 (hereinafter referred to as JS45) as reported by He, Z., Davis, J. K. and Spain, J. C., in Journal of Bacteriology, Vol.180, No. 17 (September 1998), p. 4591–4595. JS45 is a *Pseudomonas pseudoalcaligenes* which is able to use nitrobenzene as the sole source of carbon, nitrogen, and energy. See Nishino, S. F. and Spain, J. C., Applied and Environmental Microbiology, Vol. 59, No. 8 (August 1993), p. 2520–2525. JS45 was deposited in the American Type Culture Collection in August, 1997, Accession number ATCC 700437. JS45 was deposited in the American Type Culture Collection Patent Deposit in January, 2002, Patent Deposit Designation PTA-3972.

2-Aminophenol 1,6-dioxygenase was also obtained from JS45 as reported by Lendenmann, U. and Spain, J. C., in Journal of Bacteriology, Vol.178, No.21 (November 1996), p. 6227–6232. Plasmid pNBZ14 containing the 2-aminophenol 1,6-dioxygenase gene of JS45 was inserted into plasmid pUC18 and the pUC18 plasmids were transferred into *E. coli* strain DH5α as reported by Davis, J. K., He, Z., Somerville, C. C. and Spain, J. C., in Arch Microbiol, 172:330–339 (1999). This article reports that the nucleotide sequence of 2-aminophenol 1,6-dioxygenase was deposited in GenBank and assigned accession no. U93363. The last 127 bp of the sequence overlap with the first 127 bp of GenBank accession no. AF036343, which contains the structural gene of 2-aminomuconic semialdehyde dehydrogenase.

*E. coli* DH5α/pNBZ14 was grown in Luria broth (Difco, Detroit, Mich., USA) containing 50 µg/ml ampicillin at 37° C. The cells were harvested by centrifugation, washed with 25 mM potassium phosphate (pH 7.0), and stored at −70° C.

Preparation of Enzymes:

Partially purified 2-aminomuconic semialdehyde dehydrogenase was obtained from JS45 as disclosed above. Cells of *E. coli* DH5α/pNBZ14 expressing 2-aminophenol 1,6-dioxygenase were suspended in phosphate buffer (25 mM, pH 7.0) and broken by two passages through a French pressure cell at 20,000 p.s.i. The suspension was centrifuged at 20,000×g for 30 min and the pellets were discarded. The crude extract was stored at −70° C. The crude extracts or a fraction that precipitated between 50% and 70% ethanol was used as the source of 2-aminophenol 1,6-dioxygenase.

Preparation and Isolation of 2-aminomuconate:

In a total of 8 ml, the initial reaction mixture contained 10 mM potassium phosphate buffer (pH 7.5), crude extracts of pNBZ14 (0.3 mg protein), partially purified 2-aminomuconic semialdehyde dehydrogenase (0.3 mg protein), and AND⁺ (1.6 μmol). The reaction was initiated by the addition of 2-aminophenol. A total of 3.2 μmol of 2-aminophenol was added slowly over 20 min. In the same time 1.5 mg more crude extract of pNBZ14 was added in three aliquots. The NADH oxidase activity in the crude extract of pNBZ14 replenished the AND⁺ reduced during the course of the reaction. The reaction was completed in 20 min. The final volume of the reaction mixture was 8.2 ml.

The reaction mixture was diluted to 24 ml with Tris-HCl buffer (final concentration: 10 mM, pH 9.5). The mixture was passed through a Centriprep-3 tube (Amicon, Beverly, Mass., USA) to remove proteins. The filtrate was loaded on a Hitrap Q column (two 5-ml columns in series, Pharmacia, Uppsala, Sweden); the column was washed with 30 ml of 10 mM Tris-HCl buffer (pH 9.5) and 2-aminomuconate was eluted with a 100-ml linear gradient of 0–0.3 M NaCl in the same buffer. 2-Aminomuconate was eluted in fractions 14 and 15 (5.0 ml each).

2.7 μmol of 2-aminomuconate was produced from 3.2 μmol of 2-aminophenol. The total amount of 2-aminomuconate after purification by Hitrap-Q column was 2.0 μmol, indicating an overall yield of 62%. The elution profile and the spectrum of fraction 15 (diluted 1/10) indicated that 2-aminomuconate was pure. The concentration of 2-aminomuconate in fraction 15 was 0.34 mM. 2-Aminomuconate was relatively stable at such concentrations, the half-life was 20 h at room temperature, and only 30% was lost when the solution was stored on ice for 50 h. Freezing and thawing of the solution at pH 9.5 (Tris-HCl) resulted in decomposition of about 2% of the material, whereas 50% was lost after similar treatment at pH 8.0 in potassium phosphate buffer.

The advantage of using crude extracts rather than partially purified 2-aminophenol 1,6-dioxygenase is that the dioxygenase in crude extracts is stable during storage. The high dioxygenase activity in crude extracts also eliminated the requirement for ferrous salt and ascorbate, which could introduce impurities in the 2-aminomuconate solution. In addition, the crude extract contained NADH oxidase activity, which not only replenished AND⁺, but also reduced the interference of NADH, which eluted just ahead of 2-aminomuconate during anion exchange chromatography.

The solution of 2-aminomuconate is sufficiently stable to allow shipment and storage frozen. Alternatively, a two-enzyme preparation and a small anion exchange column as well as related chemicals could be supplied as a kit to produce the chemical immediately prior to use.

The availability of 2-aminomuconate will facilitate biomedical research of the metabolism and physiological functions of 2-aminomuconate in mammalian tissues, especially in the central nervous system. The activities of the oxidative metabolism of tryptophan have been linked to some abnormal inflammatory neurological conditions, such as those caused by traumatic injury to the spinal cords and ischemic brain injury to animal models. The biomedical investigation of the function of 2-aminomuconate in the pathway may lead to discovery of new therapeutic approaches of the neurological disorders caused by related injuries.

Having thus described exemplary embodiments of the present invention, it should be noted by those skilled in the art that the disclosures herein are exemplary only and that alternatives, adaptations and modifications may be made within the scope of the present invention.

We claim:

1. A method for the preparation of 2-aminomuconate from 2-aminophenol which comprises adding 2-aminophenol to a mixture of 2-aminophenol 1,6-dioxygenase, 2-aminomuconic semialdehyde dehydrogenase and AND⁺ in a buffer, and recovering a fraction containing 2-aminomuconate from the mixture, wherein said 2-aminophenol 1,6-dioxygenase is obtained by culturing *Pseudomonas pseudoalcaligenes* JS45, obtaining plasmid pNBZ14 containing the 2-aminophenol 1,6-dioxygenase gene of JS45, inserting said plasmid pNBZ14 into plasmid pUC18, transferring the resulting pUC18 plasmid into *E. coli* strain DH5α, and growing the resulting *E. coli* DH5α/pNBZ14.

2. The method of claim 1 wherein said 2-aminomuconic semialdehyde dehydrogenase is obtained by culturing *Pseudomonas pseudoalcaligenes* JS45.

3. The method of claim 1 wherein said 2-aminophenol is added to said mixture of 2-aminophenol 1,6-dioxygenase, 2-aminomuconic semialdehyde dehydrogenase and AND⁺ over a time span of 5 to 50 minutes.

* * * * *

UNITED STATES PATENT AND TRADEMARK OFFICE
CERTIFICATE OF CORRECTION

PATENT NO.    : 6,432,683 B1  
DATED         : August 13, 2002  
INVENTOR(S)   : Zhongqi He et al.

It is certified that error appears in the above-identified patent and that said Letters Patent is hereby corrected as shown below:

Column 2,
Line 12, "AND+" should read -- $NAD^+$ --.

Column 3,
Lines 1, 6 and 40, "AND+" should read -- $NAD^+$ --.

Column 4,
Lines 26 and 41, "AND+" should read -- $NAD^+$ --.

Signed and Sealed this

Seventh Day of January, 2003

JAMES E. ROGAN
*Director of the United States Patent and Trademark Office*